(12) United States Patent
Chang

(10) Patent No.: US 9,353,881 B2
(45) Date of Patent: May 31, 2016

(54) ISOLATED ELECTRICALLY-CONTROLLED VALVE

(71) Applicant: Hsu-Hui Chang, New Taipei (TW)

(72) Inventor: Hsu-Hui Chang, New Taipei (TW)

( * ) Notice: Subject to any disclaimer, the term of this patent is extended or adjusted under 35 U.S.C. 154(b) by 25 days.

(21) Appl. No.: 14/457,134

(22) Filed: Aug. 12, 2014

(65) Prior Publication Data

US 2016/0047484 A1   Feb. 18, 2016

(51) Int. Cl.
*F16K 31/06*   (2006.01)
*F16K 7/14*   (2006.01)

(52) U.S. Cl.
CPC .............. *F16K 31/0675* (2013.01); *F16K 7/14* (2013.01)

(58) Field of Classification Search
CPC .............. F16K 1/42; F16K 1/44; F16K 7/14; F16K 25/00; F16K 31/06; F16K 31/0655; F16K 1/36; F16K 27/029; F16K 27/048; F16K 31/02; F16K 31/0624; F16K 31/0641; F16K 31/0672
USPC ................ 251/129.15, 129.17, 333, 359, 366
See application file for complete search history.

(56) References Cited

U.S. PATENT DOCUMENTS

| | | | |
|---|---|---|---|
| 6,609,698 B1* | 8/2003 | Parsons | F16K 7/14 251/129.07 |
| 8,387,827 B2* | 3/2013 | Helf | A01M 1/2038 222/402.21 |
| 2013/0168584 A1* | 7/2013 | Tung | F16K 1/42 251/129.15 |

* cited by examiner

*Primary Examiner* — Matthew W Jellett
(74) *Attorney, Agent, or Firm* — Leong C. Lei

(57) ABSTRACT

An isolated electrically-controlled valve includes a base and a solenoid device. The base includes a first connection port formed on a side thereof, a second connection port formed on a bottom thereof, a coupling section extending therefrom, and a plurality of passages formed therein to allow the first and second connection ports and the coupling section to communicate with each other. The solenoid device is coupled to the first connection port and includes an isolation airtight seal gasket arranged between the base and the solenoid device. As such, the solenoid device drives the isolation airtight seal gasket to move in order to control the communication established between the second connection port and the coupling section and the isolation airtight seal gasket provides isolation between the base and the solenoid device to prohibit fluid or liquid flowing in the interior of the base from invading into the solenoid device.

6 Claims, 5 Drawing Sheets

ISOLATED ELECTRICALLY-CONTROLLED VALVE

TECHNICAL FIELD OF THE INVENTION

The present invention generally relates to an isolated electrically-controlled valve, and more particularly to an isolated electrically-controlled valve that prevents gas or liquid from invading a solenoid device.

DESCRIPTION OF THE PRIOR ART

To eliminate odd smells generated in household living spaces, such as bathroom and kitchen, various fresheners and aromatic agents are available in the market, allowing users to timely spray into air for improving the quality of the air and also to relax the stresses and pressures of the user.

The early-day products of the fresheners were generally provided for being statically placed in for example a refrigerator, a shoe chest, a bathroom, and a kitchen for eliminating or suppressing the odd smells. With the development of technology, an automatic aromatic sprayer, which provides a function of automatic spraying, is available. For example, Taiwan Utility Model M342170 discloses an "improved structure of aromatic spraying device", which generally comprises a pressurized container and a solenoid valve. The pressurized container receives therein an aromatic agent to be sprayed. The pressurized container comprises a press-down nozzle. The solenoid valve is coupled to the nozzle of the pressurized container. The solenoid valve comprises a mounting seat that comprises a passage exactly opposing the nozzle. A movable member and a spring that can be driven by a magnetic member are arranged in the passage to control opening and closing of the valve. The solenoid valve is used for operation in a noise-free and quiet manner. The solenoid valve can be operated to precisely control the duration of spraying and the amount of the aromatic agent sprayed.

However, the known patent document discloses that the solenoid valve is directly mounted to the nozzle of the pressurized container to allow the aromatic contained in the pressurized container to flow into the passage. This arrangement, however, may keep residues of the aromatic in the passage of the solenoid valve so that the movable member and the spring, as well as other components, such as a sealing gasket, may get the aromatic to attach thereto. Once the accumulation of the residual aromatic gets large, the passage of the solenoid valve may be blocked, leading to an undesired situation where the aromatic agent contained in the pressurized container is prevented from flowing out.

SUMMARY OF THE INVENTION

The primary object of the present invention is to disclose an isolated electrically-controlled valve, which comprises a base and a solenoid device. The base comprises a first connection port formed on a side thereof and a second connection port formed on a bottom thereof. The base comprises a coupling section extending from a top thereof. The base comprises a plurality of passages formed therein to allow the first connection port, the second connection port, and the coupling section to communicate with each other. The solenoid device is coupled to the first connection port formed on the side of the base and comprises an isolation airtight seal gasket arranged between the base and the solenoid device. As such, the solenoid device drives the isolation airtight seal gasket to move in order to control the communication established between the second connection port and the coupling section, allowing a spray agent to flow through the second connection port into the interior of the base and then discharge through the coupling section. Further, the isolation airtight seal gasket provides isolation between the base and the solenoid device to prohibit the agent flowing in the interior of the base from invading into the interior of the solenoid device.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
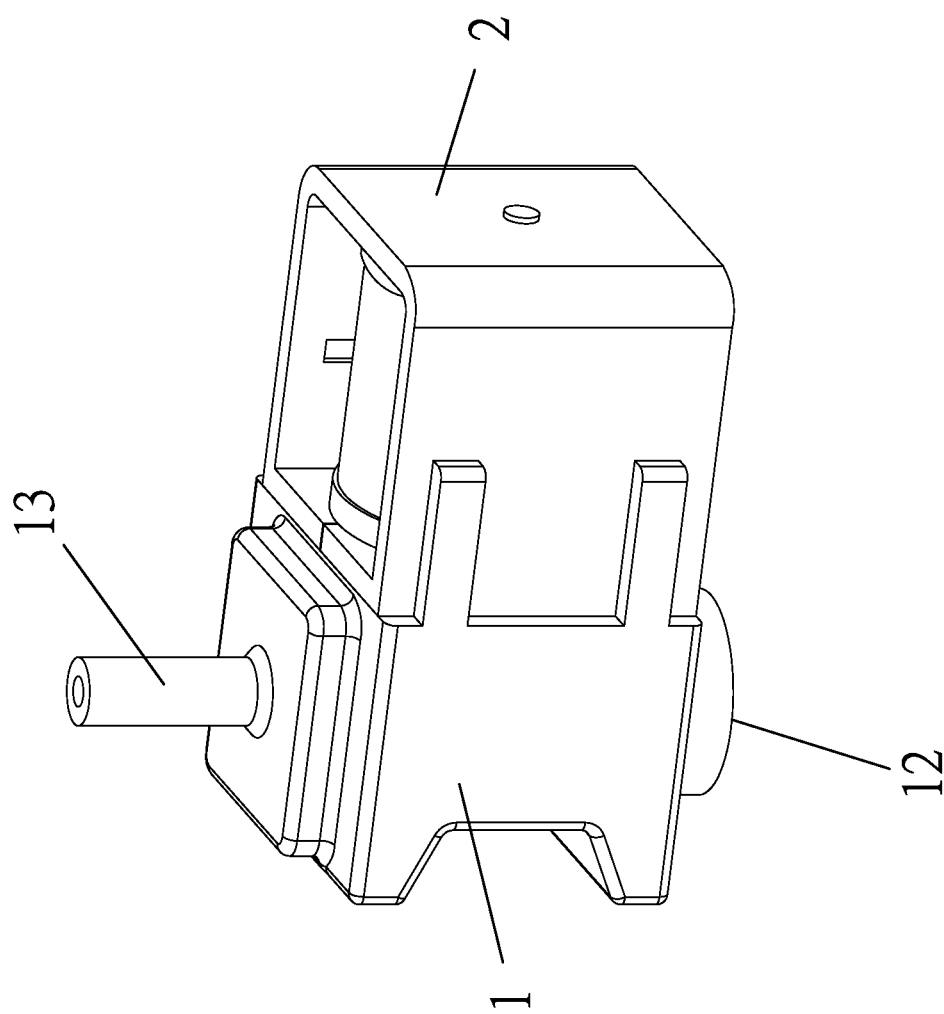
FIG. 1 is a perspective view showing an isolated electrically-controlled valve according to the present invention.
Figure 2:
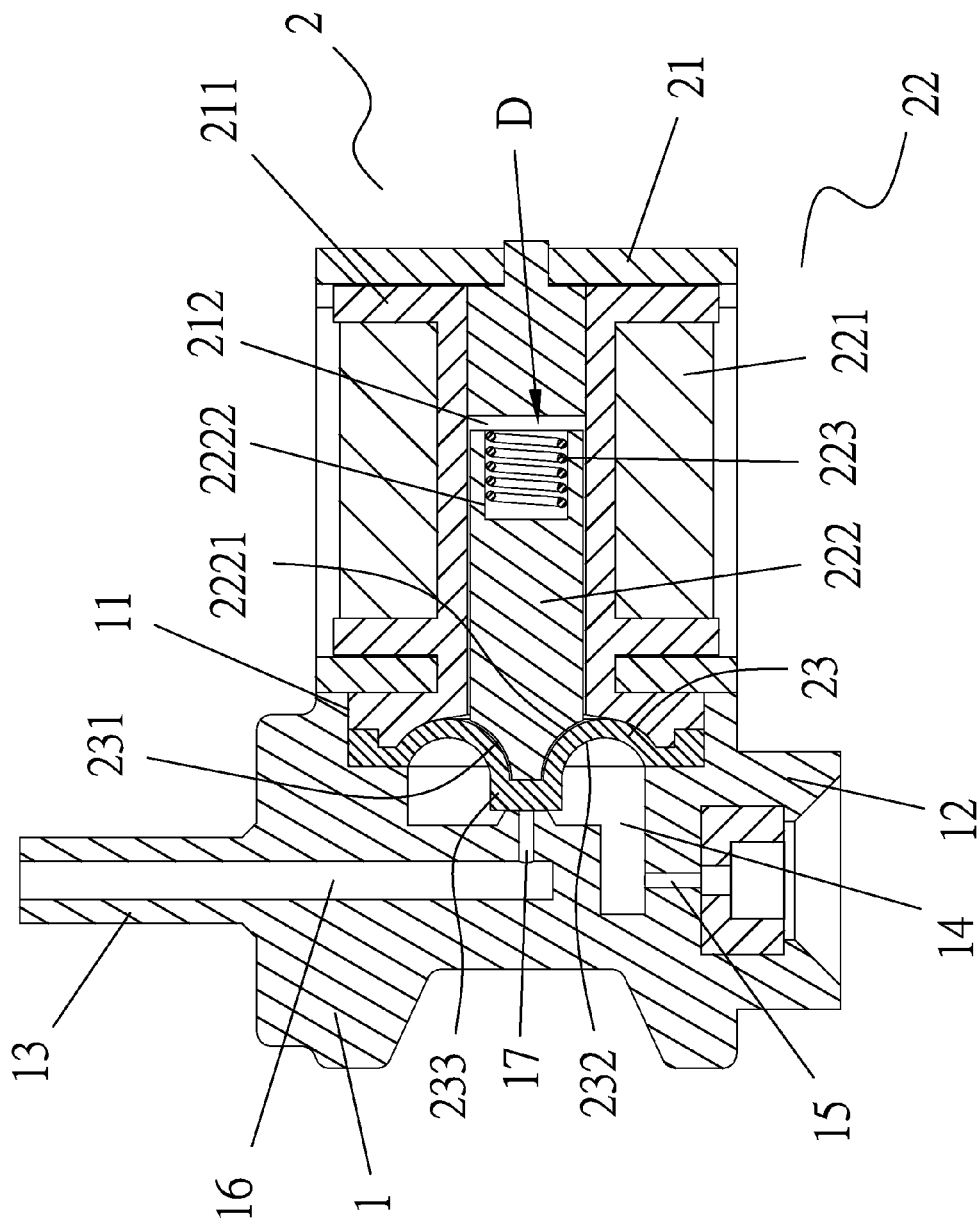
FIG. 2 is a schematic view showing a closed condition of the isolated electrically-controlled valve according to the present invention.
Figure 3:
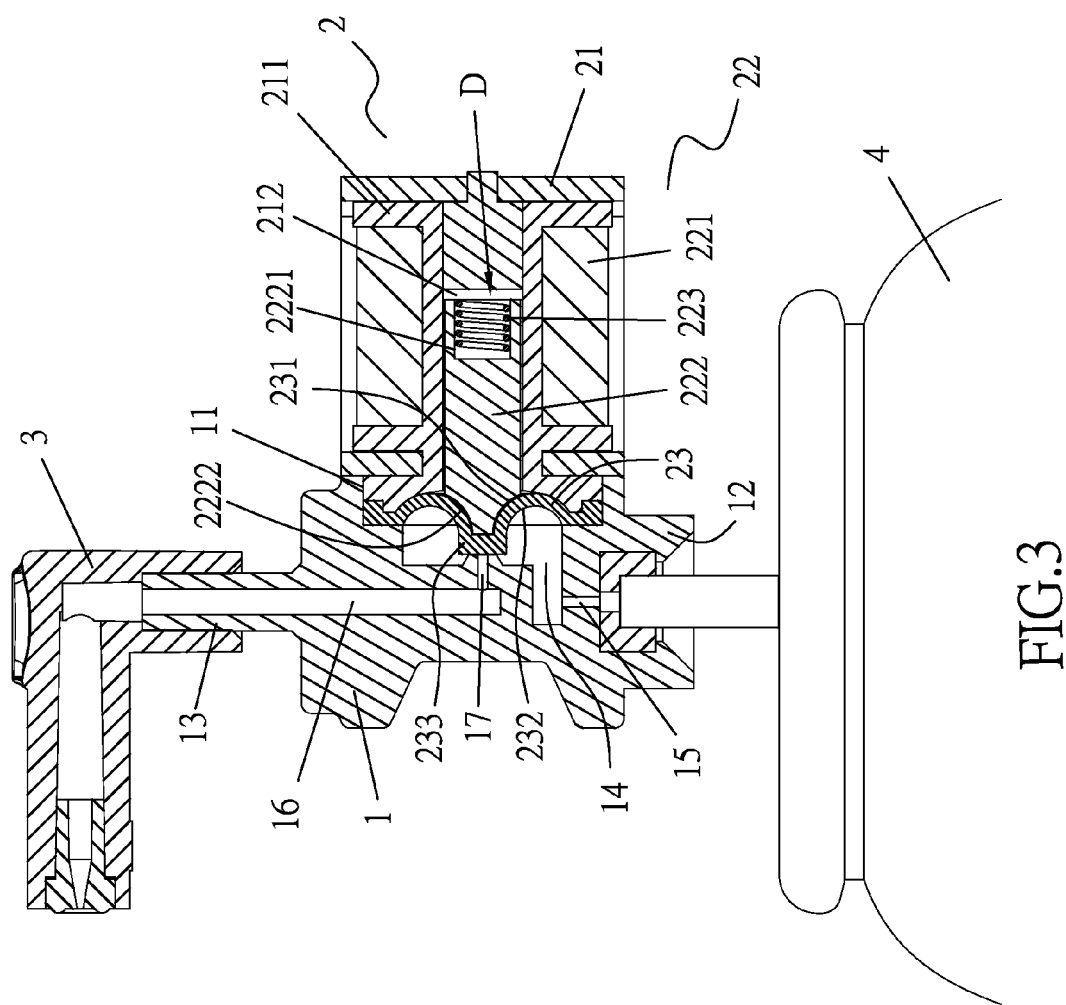
FIG. 3 is a schematic view showing a first example of application of the isolated electrically-controlled valve according to the present invention.
Figure 4:
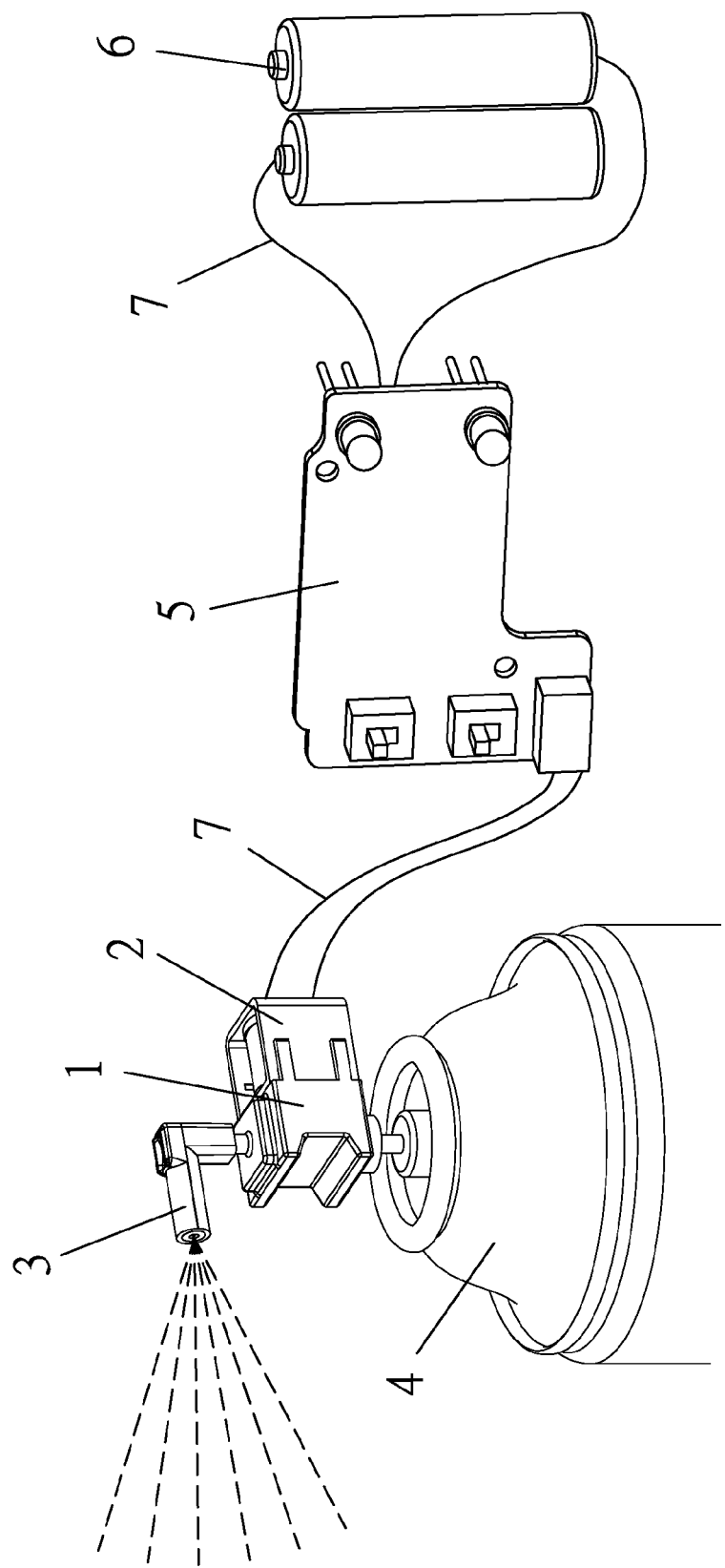
FIG. 4 is a schematic view showing a second example of application of the isolated electrically-controlled valve according to the present invention.
Figure 5:
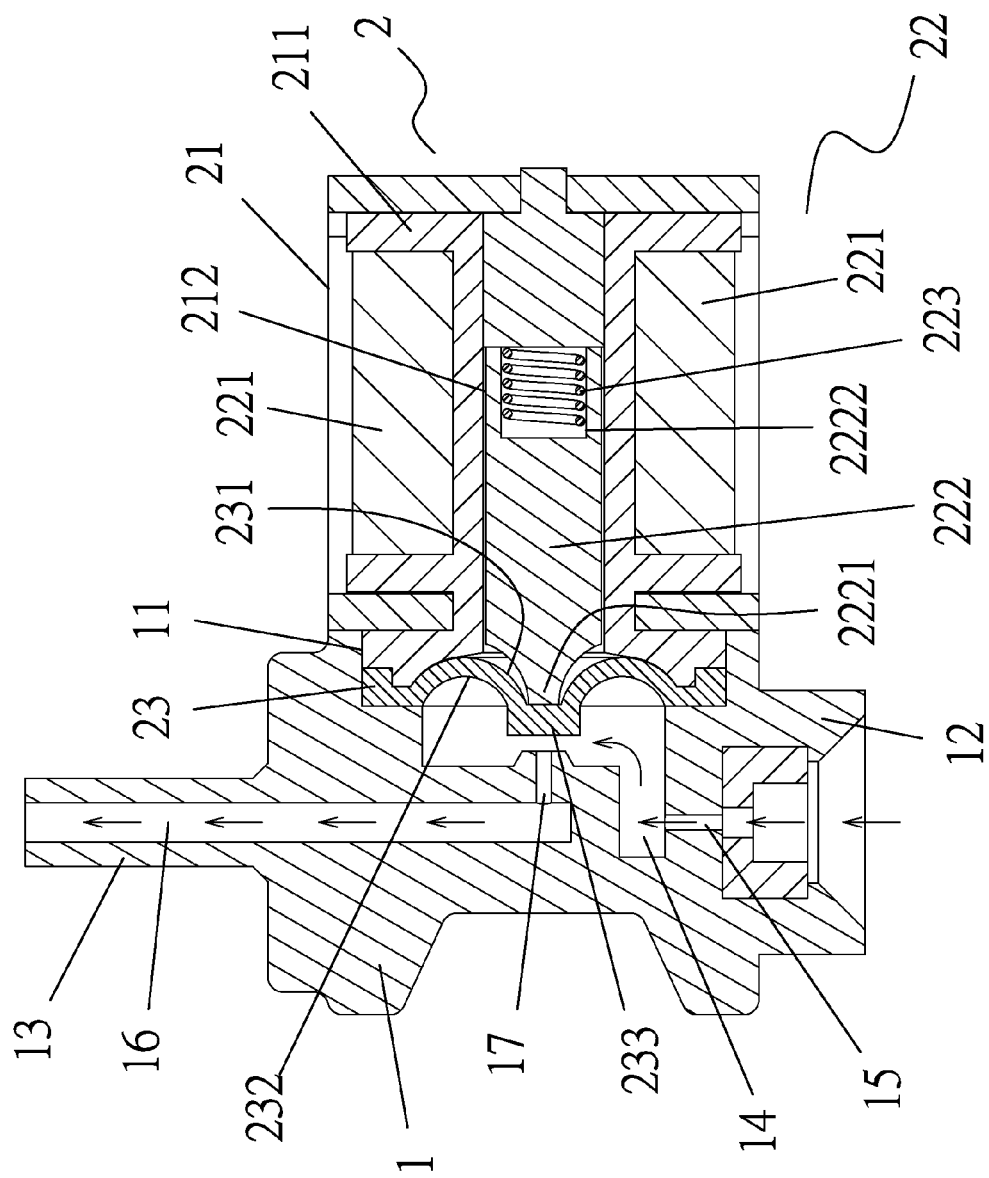
FIG. 5 is a schematic view showing an open condition of the isolated electrically-controlled valve according to the present invention.

Referring to FIGS. 1-5, the present invention discloses an isolated electrically-controlled valve, which comprises a base 1 and a solenoid device 2.

The base 1 comprises a first connection port 11 formed on a side thereof and a second connection port 12 formed on a bottom thereof. The base 1 also comprises a coupling section 13 extending outward from a top thereof. The base 1 comprises a first passage 14, a second passage 15, a third passage 16, and a fourth passage 17 formed therein. The first passage 14 is in communication with the first connection port 11. The second passage 15 is arranged between and in communication with the first passage 14 and the second connection port 12 so that the first passage 14 is set in communication with the second connection port 12. The third passage 16 extends through the base 1 and the interior of the coupling section 13. The fourth passage 17 is arranged between the first passage 14 and the third passage 16 to allow the first passage 14 to communicate with the third passage 16. As such, the second connection port 12 is set in communication, sequentially through the second passage 15, the first passage 14, and the fourth passage 17, with the third passage 16.

The solenoid device 2 is coupled to the first connection port 11 formed on the side of the base 1 in a hermetically sealed manner and comprises a solenoid seat 21, a control mechanism 22, and an isolation airtight seal gasket 23.

The solenoid seat 21 comprises a frame 211 arranged therein. The frame 211 forms a receiving space 212 and the receiving space 212 has an opening that corresponds to the first connection port 11 of the base 1.

The control mechanism 22 is arranged in the solenoid seat 21 and comprises a coil 221, a metal core 222, and an elastic element 223. The coil 221 is wound around outside and around the frame 211 of the solenoid seat 21. The metal core 222 is received in the receiving space 212 of the frame 211. The metal core 222 has an end in which a recess 2221 is formed and an opposite end on which a projection 2222 is formed. The recess 2221 of the metal core 222 is located within the receiving space 212 and the projection 2222 of the metal core 222 projects outside the receiving space 212 to correspond to the first passage 14 of the base 1. The elastic element 223 is arranged in the receiving space 212 of the frame 211 in such a way that an end of the elastic element 223 engages an inner end of the receiving space 212 and an opposite end of the elastic element 223 engages the recess 2221 of the metal core 222 so as to have the metal core 222 and the inner end of the receiving space 212 form a spacing distance D therebetween.

The isolation airtight seal gasket 23 is arranged between the base 1 and the solenoid device 2 at a position corresponding to the first connection port 11. The isolation airtight seal gasket 23 has a first surface 231 and a second surface 232. The first surface 231 faces the control mechanism 22, so that the projection 2222 of the metal core 222 of the control mechanism 22 is allowed to compress the first surface 231; and the second surface 232 faces the first passage 14 of the base 1. The isolation airtight seal gasket 23 comprises a closure block 233 formed on the second surface 232. The closure block 233 is drivable to press against and close an opening formed at an end of the fourth passage 17.

An example of application of the present invention will be described. The coupling section 13 of the base 1 is fit and thus coupled to a nozzle 3 and the second connection port 12 of the base 1 is coupled to a mist spraying can 4 in such a way that the second connection port 12 is fit to a spraying tube of the mist spraying can 4. When the solenoid device 2 is set in an open or actuated condition (see FIGS. 3 and 5), the coil 221 generates a magnetic force that pulls the metal core 222 to move toward an inner end of the receiving space 21 so that the closure block 233 of the isolation airtight seal gasket 23 disengages from the fourth passage 17, whereby a spray agent contained in the mist spraying can 4 is allowed flow (as indicated by arrows of FIG. 5) through the second connection port 12 of the base 1, then sequentially through the second passage 15, the first passage 14, the fourth passage 17, and the third passage 16, to eventually discharge through the nozzle 3. Further, when the solenoid device 2 is set in a closed or de-actuated condition, the coil 221 does not generate a magnetic force and a returning spring force of the elastic element 223 drives the metal core 222 to move in a direction toward the first passage 14 of the base 1 so as to have the closure block 233 of the isolation airtight seal gasket 23 press against and tightly engage and thus close the fourth passage 17. Since the opening of the fourth passage 17 is closed, the spray agent contained in the mist spraying can 4 is prohibited from discharging through the nozzle 3.

As such, through using the solenoid device 2 to move the isolation airtight seal gasket 23, communication between the second connection port 12 and the coupling section 13 can be selectively established, allowing the agent to flow through the second connection port 12 into the interior of the base 1 to be finally discharged through the coupling section 13. Further, the isolation airtight seal gasket 23 provides isolation between the base 1 and the solenoid device 2 so that the agent flowing through the base 1 is prohibited from invading into the interior of the solenoid device 2 thereby ensuring components arranged inside the solenoid device 2 are prevented from getting attached with the agent.

The solenoid device 2 may alternatively be electrically connected through electrical wires 7 with a control circuit 5. The control circuit 5 may be electrically connected through additional electrical wires 7 to a power supply module 6, whereby the power supply module 6 supplies electrical power to the control circuit 5 and the control circuit 5 control the solenoid device 2 to switch between an open condition and a closed condition.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An isolated electrically-controlled valve, comprising:

a base, which comprises a first connection port formed on a side thereof and a second connection port formed on a bottom thereof, the base further comprising a coupling section extending outward therefrom, the base comprising a first passage, a second passage, a third passage, and a fourth passage formed therein, the first passage being in communication with the first connection port, the second passage being arranged between and in communication with the first passage and the second connection port so that the first passage is set in communication with the second connection port, the third passage extending through the interior of the coupling section, the fourth passage being arranged between the first passage and the third passage to allow the first passage to communicate with the third passage; and a solenoid device, which is coupled to the first connection port formed on the side of the base in a hermetically sealed manner, the solenoid device comprising:

a solenoid seat;

a control mechanism, which is arranged in the solenoid seat; and an isolation airtight seal gasket, which is arranged between the base and the solenoid device at a position corresponding to the first connection port, the isolation airtight seal gasket having a first surface and a second surface, the first surface facing the control mechanism so that the control mechanism is allowed to compress the first surface, the second surface facing the first passage, the isolation airtight seal gasket comprising a closure block formed on the second surface, the closure block being drivable to press against and close fourth passage, wherein the first passage has an expanded end forming an open compartment in the first connection port and the fourth passage has an open end formed in a bottom of the compartment and in communication with the compartment, the isolation airtight seal gasket being arranged between the base and the solenoid device to cover the open compartment such that the closure block of the isolation airtight seal gasket partly projects into the open compartment to correspond to the open end of the fourth passage and a remaining portion of the isolation airtight seal gasket located outside the compartment and corresponding to the first passage, wherein the closure block of isolation airtight seal gasket is movable in the compartment to contact and close the open end of the fourth passage with the first passage that corresponds to the remaining portion of the isolation airtight seal gasket kept open and maintaining in communication with the compartment.

2. The isolated electrically-controlled valve according to claim 1, wherein the solenoid seat comprises a frame arranged therein, the frame forming a receiving space; and the control mechanism comprises a coil, a metal core, and an elastic element, the coil being wound around outside and around the frame, the metal core being received in the receiving space of the frame, the metal core having an end in which a recess is formed and an opposite end on which a projection is formed, the recess being located within the receiving space, the projection projecting outside the receiving space to correspond to the first passage of the base, the elastic element being arranged in the receiving space of the frame in such a way that an end of the elastic element engages an inner end of the receiving space and an opposite end of the elastic element engages the recess of the metal core, the metal core and the inner end of the receiving space forming a spacing distance therebetween.

3. The isolated electrically-controlled valve according to claim 2, wherein the projection of the metal core is operable to press against the first surface of the isolation airtight seal gasket.

4. The isolated electrically-controlled valve according to claim 1, wherein the coupling section of the base is adapted to couple to a nozzle.

5. The isolated electrically-controlled valve according to claim 1, wherein the second connection port of the base is adopted to connect to a mist spraying can.

6. The isolated electrically-controlled valve according to claim 1, wherein the solenoid device is electrically connected to a control circuit with electrical wires connected between the control circuit and the solenoid device, the control circuit being electrically connected to a power supply module.

* * * * *